(12) United States Patent
Fukao et al.

(10) Patent No.: US 6,784,316 B2
(45) Date of Patent: Aug. 31, 2004

(54) PURIFICATION METHOD OF CYCLOHEXANONE-OXIME

(75) Inventors: Masami Fukao, Ritto-Town (JP); Francesco Cainelli, Padua (IT); Roberto Tessari, Mirano (IT); Piero Furlan, Treviso (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 10/180,021

(22) Filed: Jun. 27, 2002

(65) Prior Publication Data

US 2003/0013916 A1 Jan. 16, 2003

(30) Foreign Application Priority Data

Jun. 28, 2001 (IT) ..................................... MI2001A1361

(51) Int. Cl.$^7$ ............................................ C07C 291/00
(52) U.S. Cl. ...................................................... 564/264
(58) Field of Search ................................. 564/264, 265

(56) References Cited

FOREIGN PATENT DOCUMENTS

| DE | 17 68 210 | 10/1971 |
| EP | 0 005 291 | 11/1979 |
| GB | 998 743 | 7/1965 |

OTHER PUBLICATIONS

Translation of DE1768210, published on Oct. 14, 1971, Schwarz et al.*

* cited by examiner

*Primary Examiner*—Samuel Barts
(74) *Attorney, Agent, or Firm*—Oblon, Spivak, McClelland, Maier & Neustadt, P.C.

(57) ABSTRACT

The invention relates to a purification method of cyclohexanone-oxime in a solution of solvents immiscible with water, which consists in washing said solutions with water or with an aqueous solution of a base having a pK<5 or in passing the solutions of cyclohexanone-oxime through a weakly alkaline ion exchange resin and, optionally, also through a weakly acid ion exchange resin.

12 Claims, No Drawings

PURIFICATION METHOD OF CYCLOHEXANONE-OXIME

The present invention relates to a purification method of cyclohexanone-oxime in solution.

Cyclohexanone-oxime is a chemical product which is used as intermediate for the production of caprolactam, whose preparation on an industrial scale can be effected by means of various processes known in the art (Ullmann's Encyclopedia, 1986, Vol.A5, pages 31–50).

An additional process, called ammoximation, is described in U.S. Pat. No. 4,745,221 and comprises the preparation of cyclohexanone-oxime by reacting cyclohexanone with ammonia and hydrogen peroxide in the presence of a catalyst having a zeolitic structure and the isomorphic substitution of a number of silicon atoms with titanium atoms (titanium silicalite or TSl).

The cyclohexanone-oxime produced by means of this method or by means of any process, however, contains non-vapourizable residues in quantities ranging from 0.01 to 0.5% by weight. These values are obtained by evaporating the oxime at 120° C. and 10 mm Hg of pressure.

The presence of these residues does not influence the subsequent transformation into caprolactam by means of Beckmann re-arrangement according to the classical industrial method in which oleum is used (Ullmann's Encyclopedia, 1986, Vol.A5, pages 31–51). The residues, on the other hand, have negative effects on the catalytic Beckmann re-arrangement carried out in vapour phase (U.S. Pat. No. 4,141,896; EP 550965).

With this latter method, the cyclohexanone-oxime which is fed in vapour phase to the reactor, must contain a negligible percentage of non-vapourizable residues.

In order to simplify the catalytic Beckmann re-arrangement, in fact, it is very important to minimize the formation of non-vapourizable solid deposits on the walls of the equipment in which the cyclohexanone-oxime is contained in vapour phase.

These deposits not only foul the apparatus walls but can also excessively foul the catalyst, thus increasing the normal number of regeneration cycles of the catalyst.

Furthermore inefficiency in the running of the catalytic re-arrangement reactor may occur making it necessary to keep the cyclohexanone-oxime in liquid state at a high temperature, in the upstream equipment, or even in vapour phase for longer times than those normally required for vapourization alone and immediate feeding to the catalytic re-arrangement reactor.

A purification method of cyclohexanone-oxime in solution has now been found which allows the content of non-vapourizable residue to be significantly reduced, consequently obtaining a product which is particularly suitable for being fed to a catalytic re-arrangement process in vapour phase.

The object of the present invention therefore relates to a purification method of cyclohexanone-oxime in a solution of solvents immiscible with water which consists in washing said solutions with water or with an aqueous solution of a base having a pK<5 or in passing the solutions of cyclohexanone-oxime through a weakly alkaline ion exchange resin and, optionally, also through a weakly acid ion exchange resin.

The method is applied to solutions of cyclohexanone-oxime dissolved in a solvent immiscible with water in which, however, the cyclohexanone-oxime has a sufficient solubility and this solubility is greater than that of cyclohexanone-oxime in water.

Solvents with these characteristics can be selected from the group consisting of aromatic hydrocarbons, cyclic or linear aliphatic hydrocarbons, chlorinated hydrocarbons, oxygenated hydrocarbons, such as for example toluene, benzene, cyclohexane, methylcyclopentane, hexane, trieline or isopropyl ether.

Toluene solutions are preferably used.

Solutions of cyclohexanone-oxime can be conveniently treated in a solvent having a content of cyclohexanone-oxime varying from 30 to 60& by weight.

The washing can be effected with water or with solutions of a base having a pK<5 or the solutions of cyclohexanone-oxime can be passed through a weakly alkaline ion exchange resin and, optionally, also through a weakly acid ion exchange resin, obtaining an analogous reduction of non-vapourizable residues.

Bases which can be used for the purposes of the present invention are, for example, selected from NaOH, KOH, $Na_2CO_3$, $NH_3$ at concentrations ranging from 0.01 N to 1 N and more conveniently from 0.05 to 0.1 N.

The volume of aqueous solution of the base used for the washing depends on the concentration of cyclohexanone-oxime present in the toluene solution and can range within a ratio of 10:1 to 1:1 parts by weight of cyclohexanone-oxime/parts by volume of solution of the base and more preferably in a ratio of 3:1 to 1:1.

The washing of the toluene solution of cyclohexanone-oxime can be effected in continuous in an appropriate column of the type used for liquid-liquid extractions or using a mixer and subsequent decanter or a series of mixers and decanters.

Solutions of cyclohexanone-oxime in toluene are, for example, obtained from the extraction section of an ammoximation process where the cyclohexanone-oxime is recovered from the hydro-alcoholic reaction mixture, after distillation of the solvent, by means of liquid-liquid extraction.

In this case, it is convenient to effect the washing of the toluene solution of cyclohexanone-oxime with an aqueous solution of NaOH having a concentration ranging from 0.05 to 0.1 N at a temperature ranging from 70 to 80° C.

After the washing, the aqueous solution of NaOH is recycled to the extraction section of the ammoximation process to recover the dissolved cyclohexanone-oxime, whereas the toluene solution of cyclohexanone-oxime is sent to the toluene stripping column from whose bottom cyclohexanone-oxime is obtained, to be used for the catalytic Beckmann re-arrangement to caprolactam.

In order to verify the washing effects of the solution of cyclohexanone-oxime, a laboratory test is used, adopting extreme thermal conditions to which the cyclohexanone-oxime can be subjected.

The cyclohexanone-oxime is heated for 5 hours to 200° C. and subsequently vapourized at 120° C. and a reduced pressure of about 10 mm Hg. After evaporation of the whole oxime, the non-vapourizable residue is quantified.

The residue is expressed as a % with respect to the quantity by weight of the oxime used for the test.

EXAMPLE 1 (Reference)

855 gr of toluene solution containing 32% by weight of cyclohexanone-oxime are subjected to distillation in a rotating evaporator at a temperature of 120° C. and a residual pressure of 100 mm Hg, until the toluene has been completely eliminated.

273.6 gr of cyclohexanone-oxime are obtained.

200 gr of said cyclohexanone-oxime are heated for 5 hours to 200° C., in a nitrogen atmosphere and after this period are distilled, in a rotating evaporator at a temperature of 120° C. and a residual pressure of 10 mm Hg. At the end of the distillation of cyclohexanone-oxime, 6.3 gr of residue remain, equal to 3.15% of the initial weight of cyclohexanone-oxime.

EXAMPLE 2

2832 gr of a toluene solution containing 850 gr of cyclohexanone-oxime are washed with 284 ml of 0.1 N aqueous solution of NaOH (ratio oxime weight/solution volume=3/1).

The washing is carried out in a stirred container, thermostat-regulated at 75° C. After 30 minutes, the stirring is stopped and the liquid is left to decant for 20 minutes. 2 phases are separated: an upper toluene phase containing cyclohexanone-oxime and a lower aqueous phase.

855 gr of toluene solution are distilled in a rotating evaporator at 120° C. and 100 mm Hg of residual pressure, until the toluene has been completely eliminated, obtaining 256 gr of cyclohexanone-oxime.

200 g of said cyclohexanone-oxime are first heated, in a nitrogen atmosphere, for 5 hours to 200° C. and subsequently distilled, in a rotating evaporator, at a temperature of 120° C. and a residual pressure of 10 mm Hg. When all of the cyclohexanone-oxime has been distilled, 1.08 gr of residue are obtained, equal to 0.54% of the initial weight of cyclohexanone-oxime.

EXAMPLES 3–8

Using the same procedure described in Example 2, further washings of toluene solutions of cyclohexanone-oxime were effected, varying the concentration of aqueous solution of NaOH and the cyclohexanone-oxime weight/volume of washing solution ratio.

The results are indicated in the following table.

EXAMPLES 9–10

These refer to washings with water effected according to the procedure described in Example 2.

TABLE

| Ex. Nr. | Wt. of cyclohexanone-oxime/Volume of washing water | Concentration of NaOH expressed as equivalents/l | Residue % after thermal test with respect to initial weight |
|---|---|---|---|
| 3 comp. | NO WASHING | / | 1.82 |
| 4 | 1/1 | 0.1 | 0.43 |
| 5 | 3/1 | 0.05 | 0.27 |
| 6 | 3/1 | 0.1 | 0.25 |
| 7 | 3/1 | 0.3 | 0.60 |
| 8 | 5/1 | 0.1 | 0.89 |

TABLE-continued

| Ex. Nr. | Wt. of cyclohexanone-oxime/Volume of washing water | Concentration of NaOH expressed as equivalents/l | Residue % after thermal test with respect to initial weight |
|---|---|---|---|
| 9 | 3/1 | $H_2O$ | 0.44 |
| 10 | 1/1 | $H_2O$ | 0.69 |

What is claimed is:

1. A purification method of cyclohexanone-oxime in a solution of solvents immiscible with water which consists in washing said solutions with an aqueous solution of a base having a pK<5 or in passing the solutions of cyclohexanone-oxime through a weakly alkaline ion exchange resin and, optionally, also through a weakly acid ion exchange resin.

2. The method according to claim 1, wherein the solvents are selected from the group consisting of aromatic hydrocarbons, cyclic or linear aliphatic hydrocarbons, chlorinated hydrocarbons, oxygenated hydrocarbons.

3. The method according to claim 2, wherein the solvents are selected from toluene, benzene, isopropyl ether, cyclohexane, methylcyclopentane, hexane, trieline.

4. The method according to claim 3, wherein the solvent is toluene.

5. The method according to claim 1, wherein the content of cyclohexanone-oxime of the solutions ranges from 30 to 60% by weight.

6. The method according to claim 1, wherein the base is selected from the group consisting of NaOH, KOH, $Na_2CO_3$, $NH_3$.

7. The method according to claim 1, wherein the aqueous solution of the base has concentrations ranging from 0.01 N to 1 N.

8. The method according to claim 7, wherein the aqueous solution of the base has concentrations ranging from 0.05 N to 0.1 N.

9. The method according to claim 1, wherein the ratio between the parts by weight of cyclohexanone-oxime contained in the solution and parts by volume of the solution of the base ranges from 10:1 to 1:1.

10. The method according to claim 9, wherein the ratio ranges from 3:1 to 1:1.

11. The method according to claim 1, wherein the washing of the solution of cyclohexanone-oxime is carried out in continuous in a suitable column or in a mixer or in a series of mixers and decanters.

12. An ammoximation process wherein the cyclohexanone-oxime in a toluene solution recovered from an extraction section of the process, is purified by means of the method according to claim 1.

* * * * *